(12) United States Patent
Sones et al.

(10) Patent No.: US 7,430,311 B2
(45) Date of Patent: Sep. 30, 2008

(54) SYSTEM AND METHOD FOR INSIDE CAN INSPECTION

(75) Inventors: Richard A. Sones, Cleveland, OH (US); Melvin L. Dick, Parma, OH (US)

(73) Assignee: Applied Vision Company, LLC, Cuyahoga Falls, OH (US)

( * ) Notice: Subject to any disclaimer, the term of this patent is extended or adjusted under 35 U.S.C. 154(b) by 680 days.

(21) Appl. No.: 11/035,415

(22) Filed: Jan. 13, 2005

(65) Prior Publication Data
US 2006/0153438 A1 Jul. 13, 2006

(51) Int. Cl.
*G06K 9/00* (2006.01)
(52) U.S. Cl. .................................. 382/143; 356/241.1
(58) Field of Classification Search .......... 382/143; 356/241.1
See application file for complete search history.

(56) References Cited

U.S. PATENT DOCUMENTS

| 4,249,075 | A | * | 2/1981 | Lovalenti | 250/223 B |
| 5,030,823 | A | * | 7/1991 | Obdeijn | 250/223 B |
| 5,699,152 | A |   | 12/1997 | Fedor et al. | |
| 5,774,212 | A | * | 6/1998 | Corby, Jr. | 356/237.2 |
| 5,912,776 | A | * | 6/1999 | Yaginuma | 359/850 |

* cited by examiner

*Primary Examiner*—Matthew C. Bella
*Assistant Examiner*—Mike Rahmjoo
(74) *Attorney, Agent, or Firm*—Hahn Loeser & Parks LLP; David J. Muzilla

(57) ABSTRACT

A system and method for imaging an interior of a substantially cylindrical object are disclosed. In accordance with an embodiment of the present invention, a substantially cylindrical illuminator is positioned above an opening of a substantially cylindrical object to be imaged (e.g., a beverage can) in order to illuminate at least a portion of the interior surface of the object. A truncated conical mirror is positioned within an interior space of the illuminator to reflect an image of at least a portion of the interior surface of the object. A single camera is positioned above the illuminator and mirror to capture a single image of at least the interior surface of the object via light reflected directly from at least a portion of the interior surface of the object to the camera and from the mirror to the camera. The entire interior surface of the object is captured in the single image which may be analyzed for defects.

29 Claims, 7 Drawing Sheets

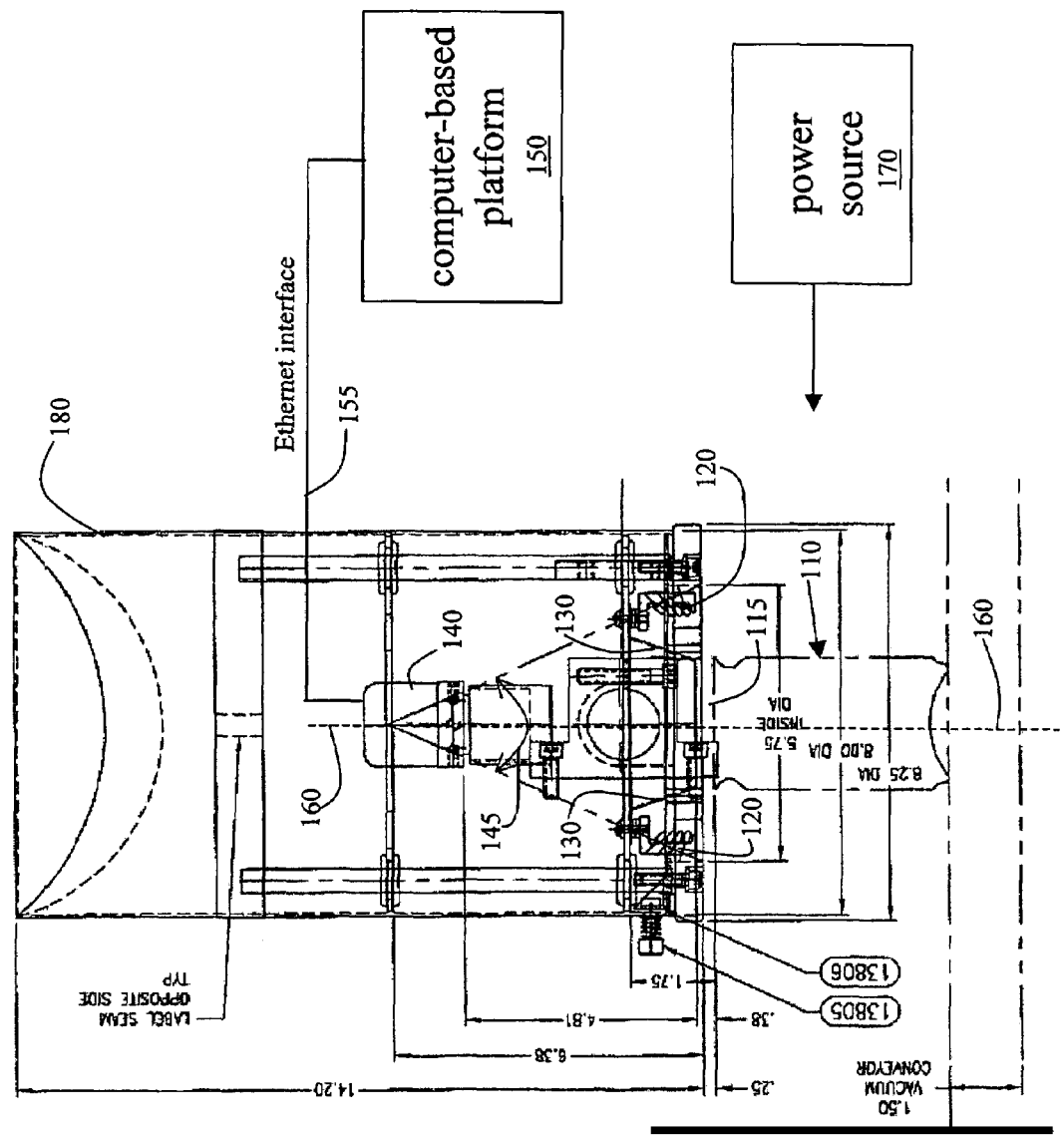

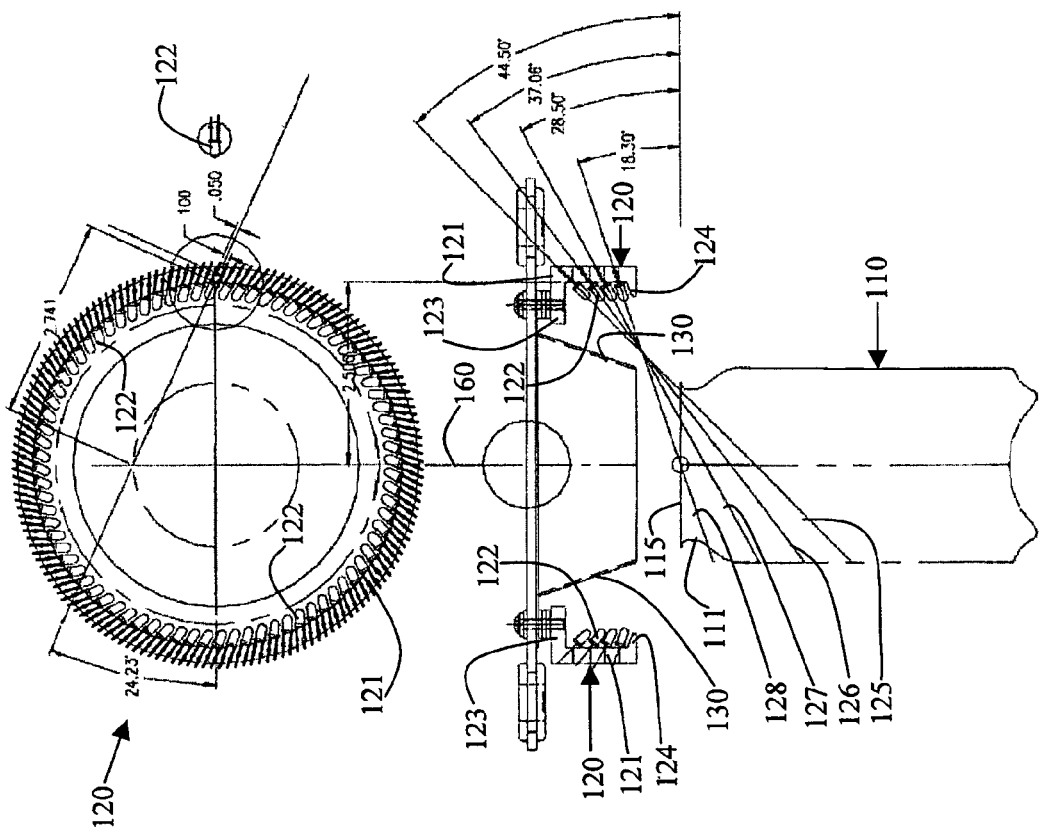

SYSTEM AND METHOD FOR INSIDE CAN INSPECTION

CROSS-REFERENCE TO RELATED APPLICATIONS/INCORPORATION BY REFERENCE

U.S. patent application Ser. No. 10/849,955, filed on May 19, 2004, is incorporated herein by reference in its entirety.

TECHNICAL FIELD

Certain embodiments of the present invention relate to automated product inspection. More particularly, certain embodiments of the present invention relate to a vision system for imaging the interior of beverage cans on a production line with at least a single camera to identify defects.

BACKGROUND OF THE INVENTION

In the beverage can industry, it is desirable to have a reliable and economical system and method for inspecting the interior surfaces of certain objects such as beverage cans and containers. Today, manufacturing processes may move, for example, aluminum beverage cans down a conveyor line at speeds of at least 2000 cans per minute. During the manufacturing of the beverage cans, defects may be formed on the interior surface of the cans. It is desirable to reject cans with such defects. Ideally, the interior surface of the cans should be free of physical defects such as puckers and dents. Also, the interior surface should be free of blistered or non-uniform coatings, oil, grease, and debris. The flanges of the cans should be free of knockdowns as well. Typically, these types of flaws occur during the manufacturing of the cans or due to contamination of the cans after manufacturing but before filling with, for example, a beverage.

Machine vision systems are typically used to inspect objects of manufacture such as beverage cans and containers. Machine vision technology allows an image of at least a portion of the object to be sensed and captured. The image may then be processed to determine if any defects are present. Typically, cameras are used to acquire images of the object and a computer or computers are used to process the image. Human vision is very good at analyzing complex objects and scenes but a human is not good at performing repeated tasks over a long period of time without tiring and making mistakes. Machine vision technology allows for sophisticated image acquisition, processing, and analysis of cans and containers on a manufacturing line and provides repeatable performance in real time.

Inspection of cans and containers via machine vision systems presents certain challenges. For example, if the cans or containers are opaque, the vision system must operate on light reflected from the surfaces of the regions to be inspected. Also, the geometry of cans and containers presents various challenges. For example, a typical metal can has a neck that extends upward and radially inward to form an open-topped neck having a smaller radius than the rest of the can. Such a design makes it harder to illuminate and image the entire interior of the can, especially around the surface of the neck of the can.

The field-of-view of cameras used for imaging are often limited and make imaging of the entire interior of an object difficult. For example, wide lens aperture cameras are often used to detect small, unacceptable defects in low light conditions. The depth of focus of a wide lens camera is typically smaller than the height of a beverage can. Therefore, to capture a good image for inspection, the region of the interior surface being imaged using a single camera is, typically, only a portion of the can. A typical beverage can, for example, has a vertical height that does not easily allow a single camera to generate a single image which captures the entire interior of the can, including the rim, neck, sides, and bottom of the can, with sharp focus.

U.S. Pat. No. 5,699,152 to Fedor et al. describes a system and method for inspecting opaque objects, such as metal beverage containers. The system includes a light source for illuminating the interior surface of the container, an ellipsoidal first mirror for forming a first image of an upper interior portion of the container, a first camera for capturing the first image of the upper interior portion of the container, a planar image-splitting second mirror for forming a second image of the flange of the container, a second camera for capturing the second image of the flange, an image combiner for electro-optically combining the first and second images, whereby a resultant composite image corresponding to substantially the entire upper interior surface of the container can be generated and analyzed for defects, a third camera located at a separate location for viewing directly the lower interior portion of the container and capturing a corresponding third image, and a computer means for analyzing the resulting images for defects. Such a system is very complicated, may be difficult to maintain, and can be rather expensive.

It is desirable to figure out how to image the entire interior of beverage cans and containers, as well as the interiors of substantially cylindrical objects in general, using at least a single camera that provides acceptable image quality to minimize cost, complexity, and maintainability of such a vision system.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

An embodiment of the present invention comprises a system for imaging an interior surface of a substantially cylindrical object. The system includes a substantially cylindrical illuminator, positioned substantially to one side of an opening of the cylindrical object to be imaged, to illuminate at least a portion of the interior surface of the cylindrical object. The system further includes a truncated conical mirror positioned substantially within the cylindrical illuminator to reflect an image of at least a portion of the interior surface of the cylindrical object. The system also includes a single camera positioned substantially to one side of the cylindrical illuminator and conical mirror to capture a single image of at least the interior surface of the cylindrical object. The single image is formed from at least light reflected directly from at least a portion of the interior surface of the cylindrical object to the camera and from the conical mirror to the camera.

Another embodiment of the present invention comprises a system for imaging an interior surface of a substantially cylindrical object. The system includes a substantially cylindrical illuminator, positioned substantially to one side of an opening of the cylindrical object to be imaged, to illuminate at least a portion of the interior surface of the cylindrical object. The system also includes a single camera positioned substantially to one side of the cylindrical illuminator to capture a single image of at least a portion of the interior surface of the cylindrical object. The single image is formed from at least light reflected directly from at least a portion of the interior surface of the cylindrical object to the camera.

A further embodiment of the present invention comprises an apparatus for illuminating at least a portion of an interior of a substantially cylindrical object. The apparatus includes an LED (light emitting diode) holder forming a substantially cylindrical surface and a plurality of LEDs positioned around and held in place by the LED holder forming a substantially cylindrical arrangement of the plurality of LEDs. An axis of illumination of each LED of the plurality of LEDs points substantially into an interior cylindrical volume circumscribed by the LED holder.

Another embodiment of the present invention comprises a method of constructing a system to image an interior surface of a substantially cylindrical object. The method comprises positioning a substantially cylindrical illuminator substantially to one side of an opening of a substantially cylindrical object to be imaged to illuminate at least a portion of an interior surface of the object. The method also includes positioning a truncated conical mirror substantially within an open interior region of the illuminator to reflect an image of at least a portion of the interior surface of the object. The method further includes positioning a single camera substantially to one side of the illuminator and the mirror to capture a single image of at least the interior surface of the object via light reflected at least directly from at least a portion of the interior surface of the object to the camera and from the mirror to the camera. The method also comprises aligning the central axes of the illuminator, the mirror, and the camera with a central axis of the object to be imaged and mounting the aligned illuminator, mirror, and camera to fix the alignment.

These and other advantages and novel features of the present invention, as well as details of an illustrated embodiment thereof, will be more fully understood from the following description and drawings.

BRIEF DESCRIPTION OF SEVERAL VIEWS OF THE DRAWINGS

FIGS. 1A and 1B illustrate an embodiment of a system for imaging an interior surface of a substantially cylindrical object, in accordance with various aspects of the present invention.

DETAILED DESCRIPTION OF THE INVENTION

Figure 2:
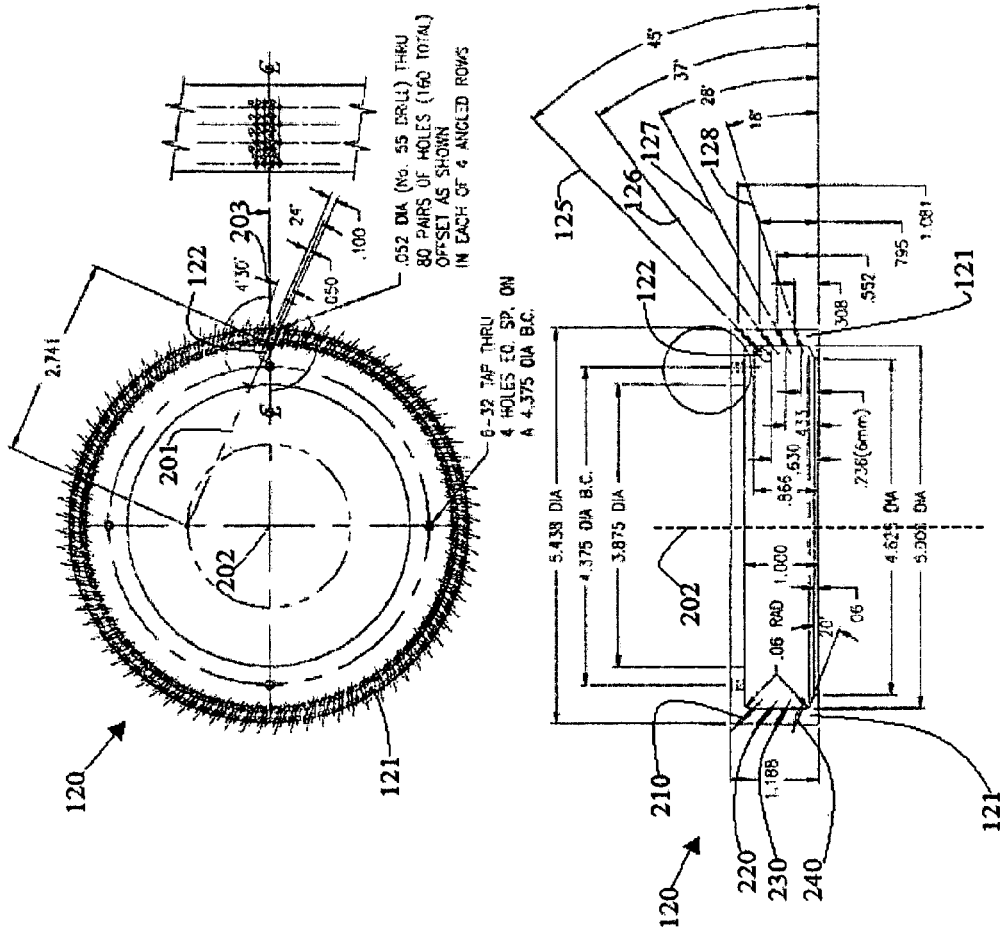
FIG. 2 illustrates an embodiment of a substantially cylindrical illuminator used in the system of FIGS. 1A and 1B, in accordance with various aspects of the present invention.

FIGS. 1A and 1B illustrate an embodiment of a system 100 for imaging an interior surface of a substantially cylindrical object 110, in accordance with various aspects of the present invention. The system 100 comprises a substantially cylindrical illuminator 120, a truncated conical mirror 130, a camera 140, and a computer-based platform 150.

The illuminator 120 is positioned to one side of (e.g., above) the object 110 to be imaged. The function of the illuminator 120 is to illuminate at least a portion of the interior surface of the object 110 (e.g., the rim or flange and neck of a beverage can). In accordance with an embodiment of the present invention, the illuminator 120 is centered above an open top 115 of a beverage can 110.

A truncated conical mirror 130 is positioned substantially within an open interior region of the illuminator 120 such that an image of at least a portion of the interior of the object 110 (e.g., the flange and neck) is reflected onto the mirror 130. The dimensions and positioning of the mirror 130 are such that the mirror 130 allows light from the illuminator 120 to enter the interior of the object 110 through an opening 115 in the object 110.

A single camera 140 is positioned substantially to one side (e.g., above) the illuminator 120 and mirror 130 such that a single image of at least the entire interior of the object 110 may be captured by the camera 140. The central axes of the camera 140, mirror 130, and illuminator 120 are all aligned along the system axis 160 which is aligned with a central axis of the object 110 to be imaged. The lens of the camera 140 is directed toward (e.g., downward) the object 110 to be imaged. The camera 140 is positioned such that a field-of-view 145 of the camera encompasses the mirror 130 and the object 110 to be imaged.

In accordance with an embodiment of the present invention, the camera 140 comprises a digital camera (e.g., a CCD camera) which interfaces to the computer-based platform 150 via an Ethernet connection 155. An image is captured digitally by the camera 140 and transferred to the computer-based platform 150 via the Ethernet interface 155. The computer-based platform 150 stores and analyzes the transferred digital image. As an alternative, the camera 140 comprises an analog camera and a frame grabber is used to capture and digitize an analog image from the camera 140. The resultant digitized image is then sent to the computer-based platform 150 as before. In accordance with a particular alternative embodiment of the present invention, the frame grabber is a part of the computer-based platform 150.

In accordance with an embodiment of the present invention, the computer-based platform 150 includes a personal computer (PC) and is used to analyze digital images from the camera 140 for defects of the interior surface of the object 110 such as, for example, puckers, dents, and knockdowns. Also, blistered or non-uniform coatings, oil, grease, and debris are also detected. The configuration of the system 100, using a single camera 140, affords a relatively small footprint that allows the system 100 to be used in relatively tight spaces.

In FIG. 1B, a relative relationship between the object 110, illuminator 120, and mirror 130 is readily apparent. Also, FIG. 1B shows a top view of the illuminator 120. In accordance with an embodiment of the present invention, the illuminator 120 comprises a substantially cylindrical light-emitting-diode (LED) holder 121. The LED holder 121 forms a substantially cylindrical surface into which a plurality of LEDs 122 may be mounted. Holes are machined into the holder 121 (two holes for each LED to be mounted) and the conductive leads of the LEDs 122 are passed through the holes in the holder 121 to position the LEDs 122 in the holder 121.

In accordance with an embodiment of the present invention, the LEDs 122 are positioned around the LED holder 121 forming four (4) rows of eighty (80) LEDs per row, stacked vertically on top of each other. The four (4) rows are horizontally oriented, each row forming a circle around the interior of the LED holder 121. The four (4) rows form a substantially cylindrical arrangement of the plurality of LEDs. For each LED 122, an axis of illumination (i.e., a line along which light is maximally transmitted from an LED) points substantially downward and into an interior cylindrical volume circumscribed by the LED holder 121. The LEDs 122 emit a spectrum of white light substantially along the axes of illumination. However, other colored LEDs may be used in accordance with various alternative embodiments of the present invention. For example, blue illumination may provide better contrast for certain defects inside a beverage can.

Even though FIGS. 1A and 1B show a vertically aligned orientation of the system 100 with the camera pointed downward, other orientations are possible as well as long as the central axes of the camera, mirror, illuminator, and object to be imaged are all aligned along a single system axis, in accordance with various embodiments of the present invention. Also, a protective enclosure 180 (see FIG. 1A) may be provided as part of the system 100, especially to protect the camera 140 and the assembly of the mirror 130 and illuminator 120.

In accordance with an alternate embodiment of the present invention, the mirror 130 is eliminated from the system 100. Such a configuration may be used to image the interior surface of an object where the camera 140 has a direct line of sight at the entire interior surface, or where it is not required to image the entire interior surface of the object, for example.

For example, in accordance with an alternative embodiment of the present invention, two separate imaging stations may be provided with each imaging station having its own camera. The first imaging station is used to image a lower interior portion of a beverage can using a single camera and a cylindrical illuminator, and a second imaging station is used to image an upper interior portion of the beverage can using a single camera, a cylindrical illuminator, and a truncated conical mirror. The two imaging stations may be in series on an inspection line. Other configurations are possible as well, using various combinations of illuminators, mirrors, and single cameras at separate imaging stations.

FIG. 2 illustrates an embodiment of a substantially cylindrical illuminator 120 used in the system 100 of FIGS. 1A and 1B, in accordance with various aspects of the present invention. Again, the illuminator 120 includes a holder 121 and a plurality of LEDs 122 forming a substantially cylindrical arrangement. A horizontal directional component of illumination 201 of each LED 122 is pointed such that the horizontal directional component of illumination 201 does not intersect an imaginary vertical central axis 202 of the interior cylindrical volume of the illuminator 120.

Also, the horizontal directional component of illumination 201 of each LED 122 is pointed at a same predetermined horizontal angle 203 (e.g., 4° 30') with respect to a horizontal directional component of illumination of an adjacent LED 122 in a same horizontally oriented row of LEDs 122 as seen in FIG. 2. As a result, the horizontal plane configuration of LEDs 122 as shown in FIG. 1B results.

Each LED 122 of the illuminator 120 also has an elevational directional component of illumination. FIG. 2 shows four (4) rows of LEDs 122 where each row corresponds to a different elevational directional component of illumination, in accordance with an embodiment of the present invention. In a first or top row 210, the LEDs 122 are pointed downward along a first elevation directional component of illumination 125 of 45° with respect to horizontal. In a second row 220, the LEDs 122 are pointed downward along a second elevational directional component of illumination 126 of 37° with respect to horizontal. In a third row 230, the LEDs 122 are pointed downward along a third elevational directional component of illumination 127 of 28° with respect to horizontal. In a fourth or bottom row 240, the LEDs 122 are pointed downward alomg a fourth elevational directional component of illumination 128 of 18° with respect to horizontal.

The compound angle formed by the horizontal directional component of illumination and the elevational directional component of illumination for each LED helps to project light an angles to produce a shadow in the captured image when a "pucker" defect is present. Such shadows allow for easier detection of the "pucker" defects by the computer-based platform 150.

As can be seen in FIG. 1B, such a configuration of LEDs 122 provide illumination of at least an upper portion of the interior of the object 110 to be imaged, including the neck 111 of the object 110 (e.g., the neck of a beverage can) to make good use of the mirror 130. However, light from the illuminator 120 also helps to illuminate the entire interior of the object 110 due to reflections of the light within the object 110.

In accordance with an embodiment of the present invention, a flexible printed circuit board (not shown) is wrapped around the outside of the LED holder 121. The conductive electrical leads of the LEDs 122 pass through holes in the LED holder 121 and holes in the flexible printed circuit board. The conductive electrical leads of the LEDs 122 are soldered to the back of the flexible printed circuit board. As a result, electrical power may be provided to the LEDs 122 via the flexible circuit board and the soldered leads help to hold the LEDs 122 in place. In accordance with an alternative embodiment of the present invention, each row of LEDs may be controlled (i.e., turned on and off) separately. Such control provides flexibility in how the interior of a beverage can is illuminated to optimize the illumination for each particular style of can.

Also, in accordance with an embodiment of the present invention, the LED holder 121 includes a first upper lip 123 and a second lower lip 124 (see FIG. 1B) to help protect the LEDs 122 from physical damage once they are mounted within the holder 121. In accordance with various embodiments of the present invention, the LED holder is made of a non-conductive, machineable, environmentally stable material such as plastic (e.g., phenolic).

The exact dimensions and parameters of the substantially cylindrical illuminator 120 and the truncated conical mirror 130 is a function of at least the type and design of the object 110 to be imaged.

In accordance with an alternate embodiment of the present invention, the substantially cylindrical illuminator may not include LEDs at all. For example, the illuminator may instead comprise a ring of neon tubing or a ring of fluorescent lighting.

Figure 3:
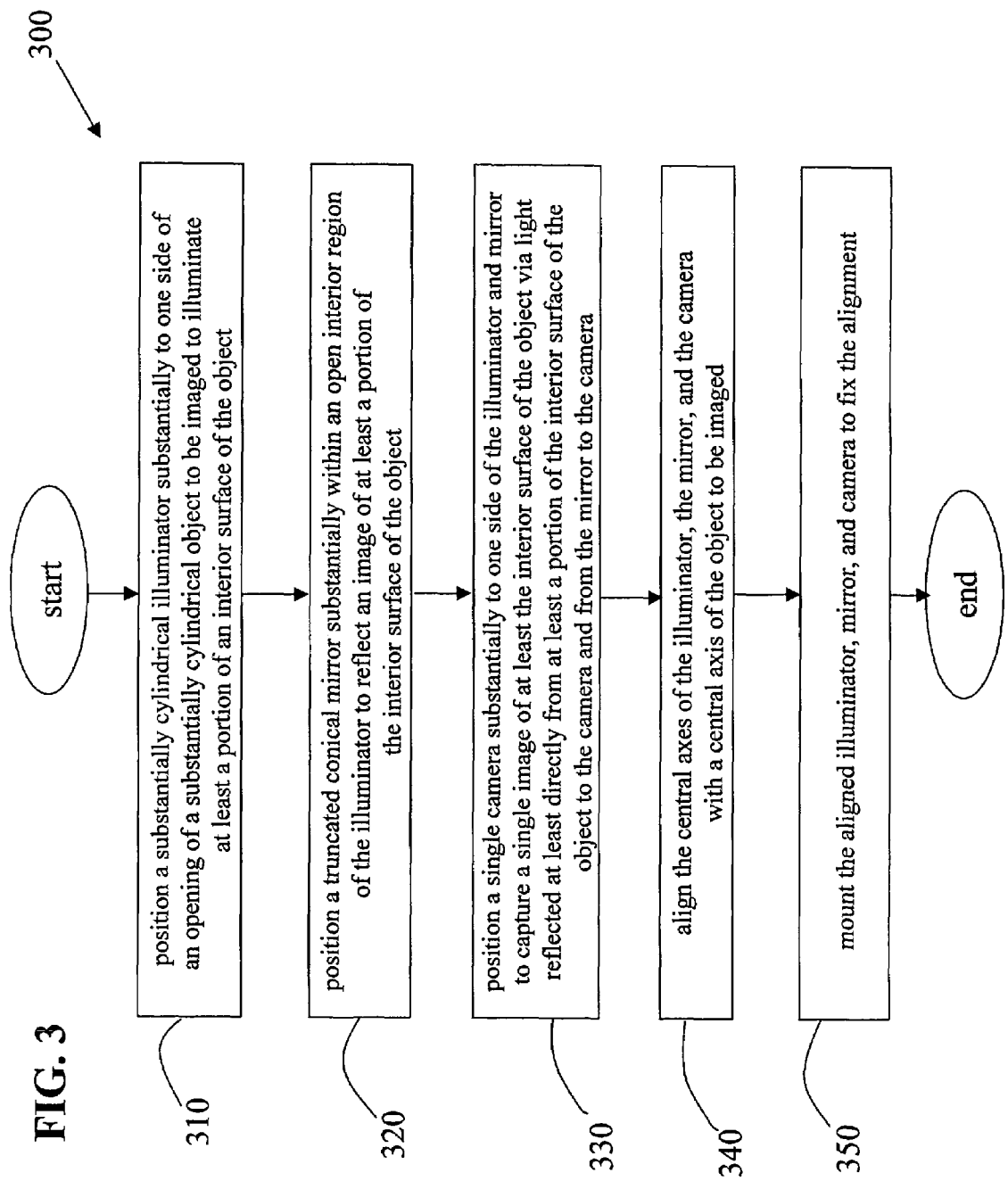
FIG. 3 illustrates an embodiment of a method to construct the system of FIGS. 1A and 1B to image an interior surface of a substantially cylindrical object, in accordance with various aspects of the present invention.

FIG. 3 illustrates an embodiment of a method 300 to construct the system 100 of FIGS. 1A and 1B to image an interior surface of a substantially cylindrical object, in accordance with various aspects of the present invention. In step 310, a substantially cylindrical illuminator is positioned to one side of an opening of a substantially cylindrical object to be imaged in order to illuminate at least a portion of the interior surface of the object. In step 320, a truncated conical mirror is positioned substantially within an open interior region of the illuminator to reflect an image of at least a portion of the interior surface of the object. In step 330, a single camera is positioned substantially to one side of the illuminator and mirror to capture a single image of at least the interior surface of the object via light reflected at least directly from at least a portion of the interior surface of the object to the camera and from the mirror to the camera. In step 340, the central axes of the illuminator, mirror, and camera are aligned with a central axis of the object to be imaged. In step 350, the aligned illuminator, mirror, and camera are mounted to fix the alignment.

The resultant orientation of the system 100 using the method 300 may be vertical, horizontal, left, right, or any other orientation, as long as the central axes are aligned as described previously. Also, the parameters of the camera 140 and exactly how the camera 140 is positioned is a function of at least the type and design of the object 110 to be imaged.

The method 300 further includes interfacing the single camera 140 to a computer-based platform 150 for storing and analyzing images. The method 300 also includes providing electrical power to the camera 140, computer-based platform 150, and illuminator 120. Electrical power may be provided by a separate power source 170 (see FIG. 1A) of the system 100 such as a power supply or battery. As an alternative, a power supply in the computer-based platform 150 can provide power for the computer-based platform 150, the camera 140, and the illuminator 120, in accordance with an embodiment of the present invention.

In a typical manufacturing/inspection environment, the system 100 is mounted over a conveyor system line which passes objects (e.g., open-topped beverage cans) past the system 100 such that the objects pass through the field-of-view 145 of the system 100. The system 100 may be synchronized to the conveyor system line such that, whenever an object 110 is entirely within the field-of-view 145 of the system 100, the system 100 captures an image and analyzes the image for defects. If an unacceptable defect is found for a particular object 110, the object 110 is purged from the conveyor system line. In accordance with an embodiment of the present invention, images are captured and analyzed fast enough such that a conveyor system line running at speeds in excess of 2000 objects per minute may be accommodated by the system 100.

Figure 4:
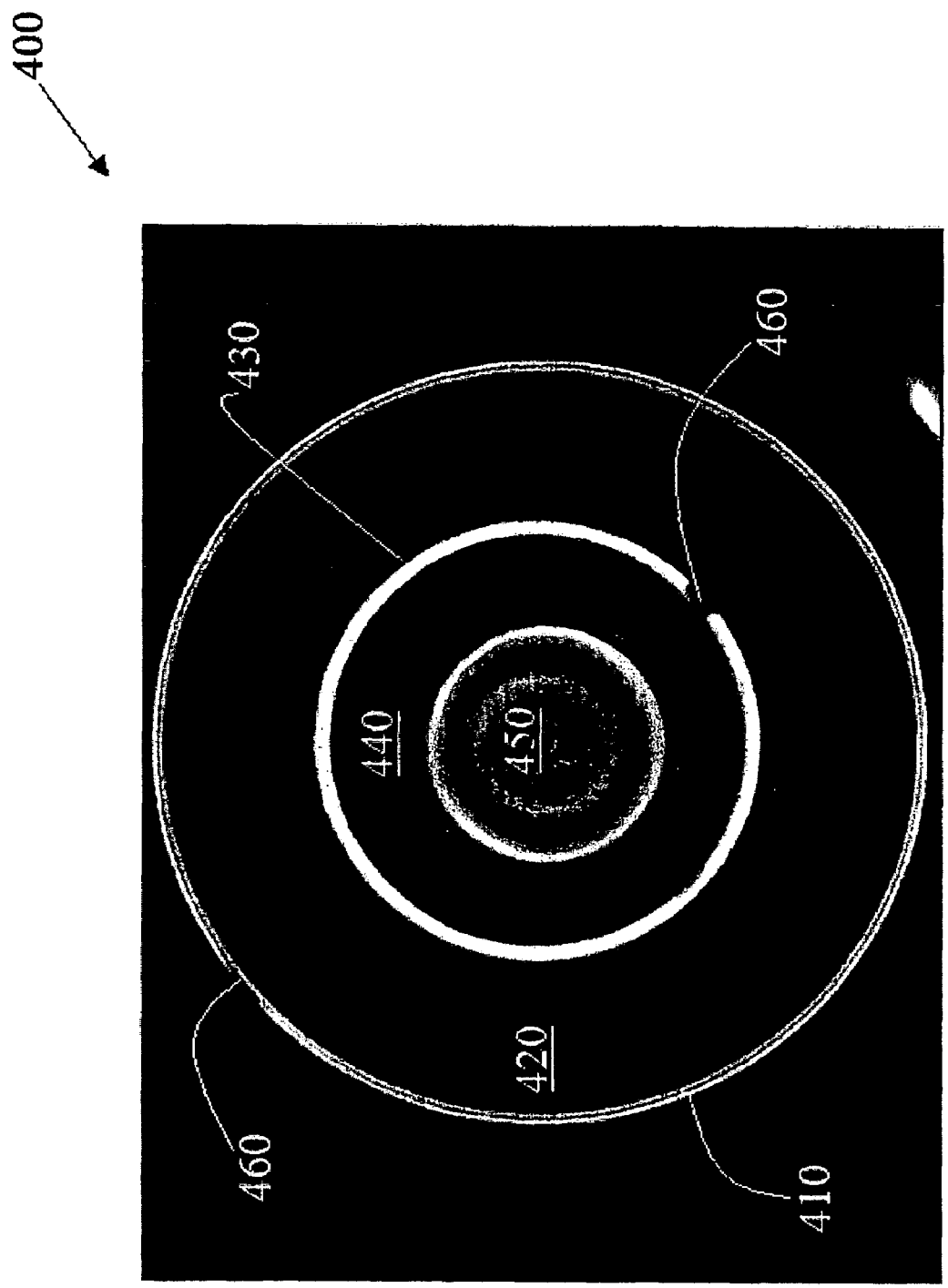
FIG. 4 illustrates an exemplary embodiment of a single image formed by the system of FIGS. 1A and 1B, in accordance with various aspects of the present invention.

FIG. 4 illustrates an exemplary embodiment of a single image 400 formed by the system 100 of FIGS. 1A and 1B, in accordance with various aspects of the present invention. The single image 400 is of a typical soda can. The image 400 includes a first part which includes the reflection of the rim or flange 410 and the upper portion 420 of the interior surface of the soda can from the truncated conical mirror 130 to the camera 140. The first part of the image is spread out by the mirror 130 (i.e., is not to scale) and images at least the rim and neck of the soda can to about 25% of the way down the vertical length of the soda can. The image 400 also includes a second part which is imaged directly from the soda can to the camera 140 and includes a reflection of the rim or flange 430, the lower portion 440 of the interior surface of the soda can, and the bottom 450 of the soda can.

The first part of the image 400, which is from the mirror 130, is an image part that corresponds to an opposite side of the soda can. For example, referring to FIG. 1B, the image appearing on the right side of the mirror 130 corresponds to the light reflected off of the left side of the interior surface of the object 110. This is true for all angles all the way around the mirror 130. Note that the rim 410 is the same rim 430 in the image 400. However, the rim 410 is spread out by the mirror 130 making it appear larger and, again, the rim 410 in the image is from the mirror and corresponds to an opposite side of the soda can.

In accordance with an embodiment of the present invention, there is an overlap region of the first part of the image 400 and the second part of the image 400. That is, a portion of the interior surface of the soda can appears twice in the image as does the rim (410 and 430). This overlap region corresponds to a transition region on the interior surface of the soda can where imaging transitions from the upper portion of the soda can using the mirror 130 to the lower portion of the soda can using the camera directly. It is desirable to have an overlap region to ensure that the entire interior surface of the soda can is imaged without any gaps between the first part of the image (which is from the mirror) and the second part of the image.

Also, it is important to remember that the image 400 is captured as a true single image and is not a composite of two or more captured images. That is, the mirror and the lower portion of the interior surface of the soda can is within the field-of-view 145 of the camera 140 such that only a single image needs to be captured to have an image of the entire interior surface of the soda can as well as the rim. In accordance with an embodiment of the present invention, the single camera 140 is a high resolution, high speed digital camera that provides digital images comprising 1000 pixels by 1000 pixels (i.e., 1 mega-pixel images).

In FIG. 4, a defect 460 can be seen in the image 400 on the rim (410 and 430) of the soda can. Notice that the defect 460 appears twice in the image. However, on the rim 410 in the image 400, the defect 460 appears on an opposite side compared to the defect 460 on the rim 430 in the image 400. Again, this is due to the reversal caused by the configuration of the mirror 130 with respect to the object to be imaged 110. It does not matter that a first part of the image 400 is spread out and reversed by the mirror 130 and that the second part of the image 400 appears inside of the first part of the image 400 from the mirror 130. The idea is not to render an image of the soda can as would be seen by a human observer looking down on the soda can without the system 100 in place. Instead, the idea is simply to obtain a single image which captures the entire interior surface of the soda can such that any significant defects may be detected.

Consider inspecting a beverage can with a wide-angle lens and a conical mirror. It is desired to inspect the flange and entire inside of the can. The flange, sidewall and bottom is imaged directly, while the neck is imaged indirectly through the conical mirror.

Figure 5:
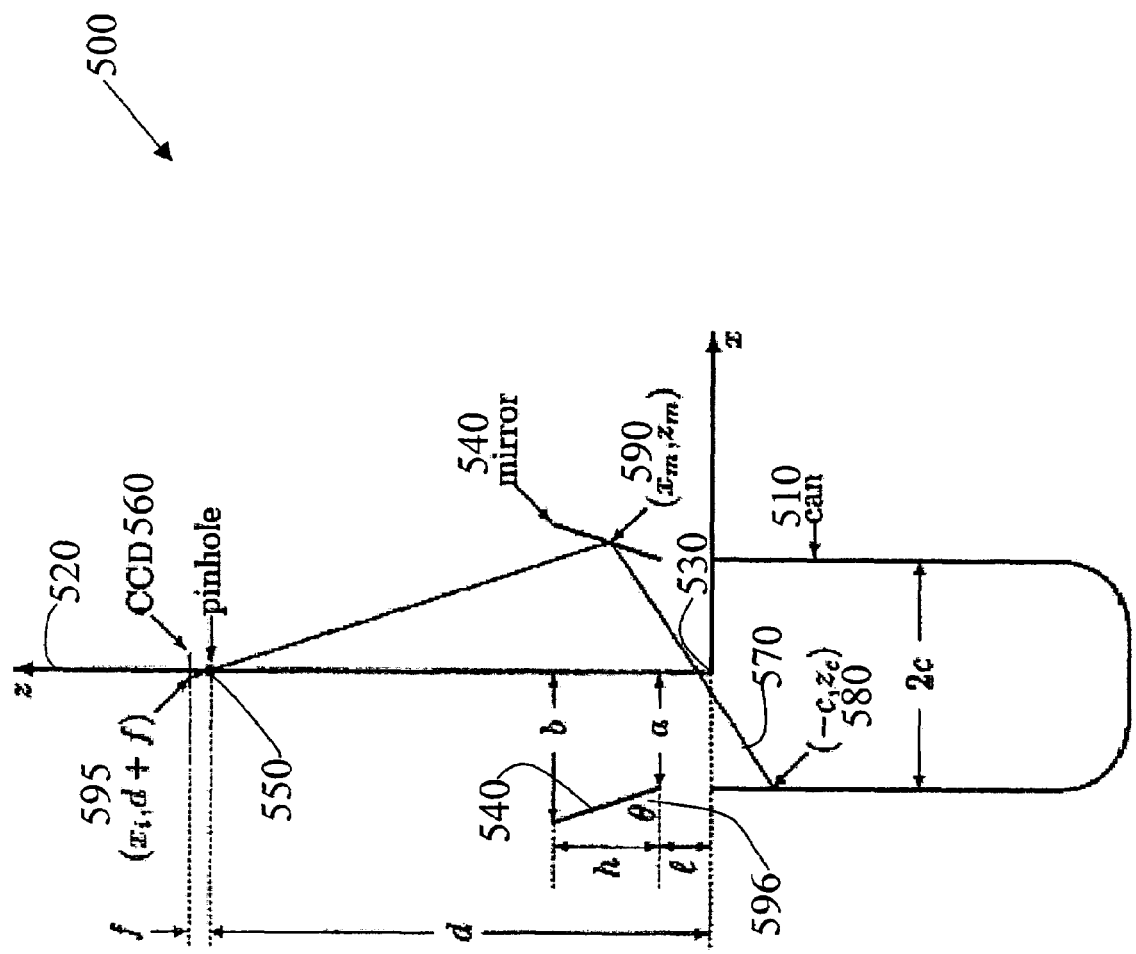
FIG. 5 illustrates an exemplary can imaging geometry, in accordance with an embodiment of the present invention.

Consider a cylindrical can 510 of radius c standing on a table (see FIG. 5). Let the unit vectors $\hat{x}\hat{y}\hat{z}$ represent a Cartesian coordinate system where $\hat{z}$ 520 coincides with the can axis and points up, and the origin 530 is coplanar with the top end of the can. Consider a funnel-shaped (conical) mirror 540 located above the can with the inside of the funnel reflective and facing up, and the cone axis along $\hat{z}$. The bottom of the mirror has radius a and is a distance l above the top of the can, and the top of the mirror has radius b and is a distance l+h above the top of the can. Finally, consider a pinhole camera 550 with its optical axis along $\hat{z}$ looking down into the mirror, with the pinhole a distance d above the top of the can and CCD surface 560 a distance f (the lens focal length) above the pinhole.

Because of the cylindrical symmetry of the can-mirror-camera system 500 and the assumption of pinhole optics, calculations can be restricted to the $\hat{x}\hat{z}$ lane. Consider a light ray 570 which emerges from a point 580

$$r_c = -c\hat{x} + z_c\hat{z} \quad (1)$$

on the inside surface of the can, then strikes the mirror surface at 590

$$r_m = x_m\hat{x} + z_m\hat{z} \quad (2)$$

and is reflected through the camera pinhole onto the image surface at 595

$$r_i = x_i \hat{x} + (d+f)\hat{z}. \tag{3}$$

Note that both $z_c$ and $x_i$ are negative, while $x_m$ and $z_m$ are positive. It will prove convenient to replace $z_c$ and $x_i$ with positive dimensionless parameters $$\alpha \equiv -z_c/c$$

$$\beta \equiv -x_i/f. \tag{4}$$

The goal is to calculate $\beta$ as a function of $\alpha$ for given a, b, c, d, f, h and l. The conical shape of the mirror imposes the constraint $$z_m = l + \gamma(x_m - a) \tag{5}$$

or $$x_m = a + \gamma^{-1}(z_m - l), \tag{6}$$

where $$\gamma \equiv \frac{h}{b-a} = \tan\Theta \tag{7}$$

and $\Theta$ is the angle 596 between the mirror surface and $\hat{x}$. The fact that the ray must pass through the pinhole imposes the constraint $$r_m + s(r_i - r_m) = d\hat{z} \tag{8}$$

where s is a real parameter. Substituting $r_m$ and $r_i$ from equations (2) and (3) into (8) and solving yields $$s = \frac{x_m}{x_m + f\beta} \tag{9}$$

and $$\beta = \frac{x_m}{d - z_m}. \tag{10}$$

Combining equations (6) and (10) gives $$\beta = \frac{\gamma a + (z_m - l)}{\gamma(d - z_m)} \tag{11}$$

or $$z_m = \frac{l - \gamma a + \gamma d\beta}{1 + \gamma\beta}. \tag{12}$$

A final constraint is that the angle of incidence must equal the angle of reflection at the mirror. This constraint may be written as $$(r_{cm}/|r_{cm}|) \cdot t_m = (r_{mi}/|r_{mi}|) \cdot t_m, \tag{13}$$

where $$r_{cm} \equiv r_m - r_c$$

$$r_{mi} \equiv r_i - r_m \tag{14}$$

and $$t_m \equiv dr_m/dx_m, \tag{15}$$

is tangent to the mirror surface at $r_m$. Substituting $r_m$ from equation (2) into (15) and using (5) gives $$t_m = \hat{x} + \frac{dz_m}{dx_m}\hat{z} = \hat{x} + \gamma\hat{z}. \tag{16}$$

Equation (13) yields multiple solutions for $\beta$, but only one in potentially positive and, thus, of physical interest:

$$\beta = \frac{c(1-\gamma^2) + 2\gamma(l-\gamma a) + 2\gamma c\alpha}{2l - 2\gamma(a+c) - d(1+\gamma^2) + c(1-\gamma^2)\alpha}. \tag{17}$$

Solving this equation for $\alpha$ yields $$\alpha = \frac{c(1-\gamma^2) + 2\gamma(l-\gamma a) - (2l - 2\gamma(a+c) - d(1+\gamma^2))\beta}{-2\gamma c + c(1-\gamma^2)\beta}. \tag{18}$$

Suppose the can radius c is given and we have selected a candidate camera-lens combination with lens focal length f and maximum image radius $\beta_{max}$ on the CCD. (Recall that image radii are expressed as fractions of f.)

The direct image of the can falls on the CCD within the radius $$\beta_0 = \frac{c}{d}. \tag{19}$$

The indirect (neck) image covers an annulus with inner radius $$\beta_1 = \frac{a}{d-l} \tag{20}$$

and outer radius $\beta_2$, where $\beta_1$ and $\beta_2$ correspond to the lowest and highest portions of the neck imaged. The indirect image must not occlude the direct image so $$\beta_1 \geq \beta_0. \tag{21}$$

To utilize the CCD efficiently, it is desired that $$\beta_1 \cong \beta_0. \tag{22}$$

In all cases of interest, the bottom of the mirror is much closer to the can than is the pinhole (l<<d), so the condition $$a = c \tag{23}$$

is a practical way to enforce (22) while still leaving a gap between $\beta_0$ and $\beta_1$ to accommodate mechanical tolerances and slight mis-centering of the can. It is desirable to image the neck all the way to the top of the can ($\alpha=0$), so from equation (17) is obtained $$\beta_2 = \frac{c(1-\gamma^2) + 2\gamma(l-\gamma a)}{2l - 2\gamma(a+c) - d(1+\gamma^2)} \tag{24}$$

which implies

-continued $$\gamma \pm = \frac{A \pm \sqrt{A^2 + BC}}{B} \quad (25)$$

where $$A \equiv l + (a+c)\beta_2 \quad (26)$$

$$B \equiv 2a + c - d\beta_2$$

$$C \equiv c + (d - 2l)\beta_2.$$

The values of $\beta_0$ and $\beta_2$ dictate how the available CCD surface is allocated to direct and indirect imaging, and they satisfy $$0 < \beta_0 < \beta_2 < \beta_{max}. \quad (27)$$

It will prove convenient to define $$\rho_0 \equiv \beta_0/\beta_{max}$$

$$\rho_2 \equiv \beta_2/\beta_{max}, \quad (28)$$

where $$0 < \rho_0 < \rho_2 < 1. \quad (29)$$

The value of l is at the disposal of the designer, so long as the assumption l<<d made in conjunction with equation (23) is satisfied. In practice l should be just large enough to avoid mechanical jams and to allow illuminating the inside of the can from below the mirror.

The design process for a conical mirror is now desired. Values of c, f and $\beta_{max}$ are given and the designer selects values of $\rho_0$, $\rho_2$ and l. Then $\beta_0$ and $\beta_2$ are determined from equations (28), d and a determined from equations (19) and (23), and the physically appropriate (positive) solution for $\gamma$ is determined from equation (25).

Consider inspecting a beverage can of radius c=33 mm using a camera-lens combination with f=6.5 mm and $\beta_{max}$=0.46 (i.e., the Jenoptik P lens and a megapixel camera). Devote 50% of the image width to the direct image ($\rho_0$=0.5) and another 40% to the indirect image ($\rho_2$=0.9). Let the bottom of the mirror be l=15 mm above the can. These equations (28) give $$\beta_0 = 0.230$$

$$\beta_2 = 0.414, \quad (30)$$

equations (19) and (23) give $$d = 143 \text{ mm}$$

$$a = 33 \text{ mm}, \quad (31)$$

and equation (25) gives $$\gamma = 2.85. \quad (32)$$

This value of $\gamma$ corresponds to a cone angle (measured from the horizontal) of $\Theta = 71°$.

The location of the top of the mirror can be calculated from equation (12) with $\beta = \beta_2$, which gives $$l + h = 41 \text{ mm} \quad (33)$$

and implies a mirror height of $$h = 26 \text{ mm}. \quad (34)$$

This is actually the minimum permissible mirror height. In practice, one should make the mirror somewhat larger, to accommodate mechanical tolerances and slight mis-centering of the can.

It is of interest to calculate how far down the neck the mirror sees. This location corresponds to (see equation (20))

$$\beta_1 = 0.257. \quad (35)$$

Substituting this value into equation (18) gives $$\alpha = 1.05. \quad (36)$$

Then from (4) we obtain $$|z_c| = 35 \text{ mm} \quad (37)$$

which is the maximum distance down the neck imaged by the mirror.

Figure 6:
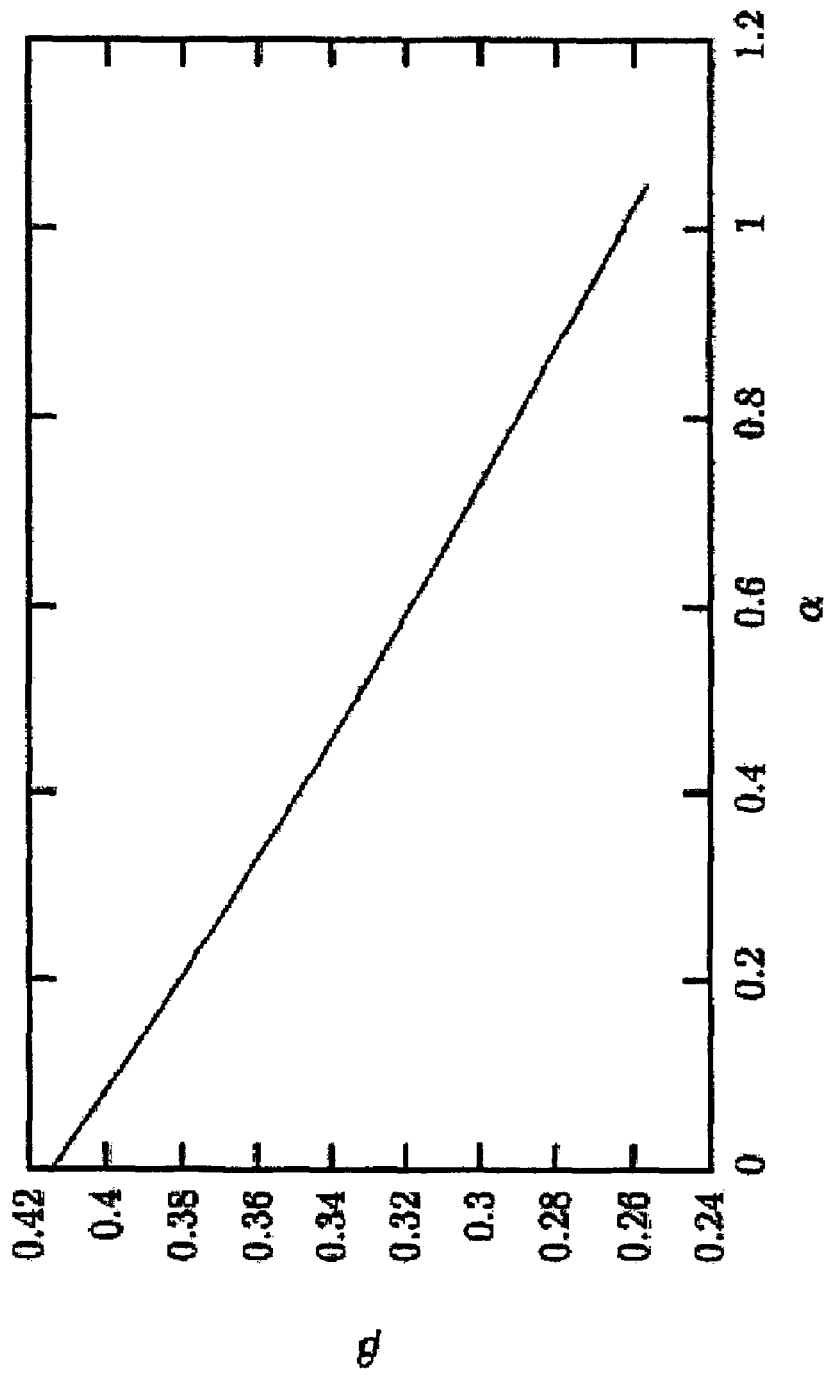
FIG. 6 illustrates an exemplary graph of radial position on a CCD corresponding to a given distance down a neck of a beverage can, in accordance with an embodiment of the present invention.

FIG. 6 is a plot of equation (17). It shows the radial location on the CCD ($\beta$) corresponding to a given distance down the can neck ($\alpha$). Recall that $\alpha$ and $\beta$ are expressed in terms of c and f, respectively. Note that the mapping from $\alpha$ to $\beta$ is nearly linear.

In summary, a system and method is disclosed for imaging the entire interior surface of a substantially cylindrical object, such as a beverage can, by capturing a single image with a single camera. The image is subsequently analyzed for defects such as dents and puckers. Such a system may be installed as part of a manufacturing line to detect defects of objects passing along the line such that the defective objects may be rejected.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A system for imaging an interior surface of at least one substantially cylindrical object, said system comprising:

a substantially cylindrical illuminator, positioned substantially to one side of an opening of a substantially cylindrical object to be imaged, to illuminate at least a portion of said interior surface of said substantially cylindrical object, wherein said substantially cylindrical illuminator includes a plurality of light emitting diodes (LEDs) arranged in rows, and wherein axes of illumination of said LEDs are pointed downward at predefined elevation angles with respect to horizontal such that each of said rows corresponds to a different predefined elevation angle;

a truncated conical mirror positioned substantially within an open interior region of said substantially cylindrical illuminator to reflect an image of at least a portion of said interior surface of said substantially cylindrical object; and a single camera positioned substantially to one side of said substantially cylindrical illuminator and said truncated conical mirror to capture a single image of at least said interior surface of said substantially cylindrical object via light reflected at least directly from at least a portion of said interior surface of said substantially cylindrical object to said camera and from said truncated conical mirror to said camera.

2. The system of claim 1 further comprising a computer-based platform interfacing to said camera to receive, in digital form, said single image.

3. The system of claim 2 wherein said computer-based platform analyzes said single image to identify any defects of at least said interior surface of said substantially cylindrical object.

4. The system of claim 2 wherein said camera interfaces to said computer-based platform via an Ethernet connection.

5. The system of claim 2 wherein said computer-based platform comprises a personal computer (PC).

6. The system of claim 1 wherein a central axis of a lens of said camera, a central axis of said truncated conical mirror, and a central axis of said substantially cylindrical illuminator are substantially aligned along a single central axis of said system.

7. The system of claim 1 wherein said substantially cylindrical object comprises a beverage can wherein a top of said beverage can is substantially open.

8. The system of claim 1 wherein said camera comprises a digital camera.

9. The system of claim 1 wherein said system images in excess of 2000 of said objects per minute as said objects pass within a field of view of said system one after another.

10. The system of claim 1 wherein said single image comprises at least 1000 pixels by 1000 pixels.

11. The system of claim 1 wherein said arrangement of said plurality of light emitting diodes comprises four horizontally stacked, circular rows of LEDs.

12. The system of claim 1 wherein said substantially cylindrical illuminator includes a substantially cylindrical. flexible printed circuit board to electrically interface to said plurality of light emitting diodes.

13. The system of claim 1 wherein an axis of illumination of each LED of said plurality of light emitting diodes points substantially into an interior cylindrical volume circumscribed by said arrangement of said plurality of light emitting diodes.

14. The system of claim 13 wherein a horizontal directional component of illumination of each LED of said plurality of LEDs, in any imaginary horizontal plane crossing through said substantially cylindrical illuminator, is pointed such that said horizontal directional component of illumination does not intersect an imaginary vertical central axis of said interior cylindrical volume.

15. The system of claim 14 wherein said horizontal directional component of illumination of said each LED is pointed at a same predetermined horizontal angle with respect to a horizontal directional component of illumination of an adjacent LED in a same horizontally oriented row of said substantially cylindrical arrangement of said plurality of LEDs.

16. A system for imaging an interior surface of at least one substantially cylindrical object, said system comprising:
  a substantially cylindrical illuminator, positioned substantially to one side of an opening of a substantially cylindrical object to be imaged, to illuminate at least a portion of said interior surface of said substantially cylindrical object, wherein said substantially cylindrical illuminator includes a plurality of light emitting diodes (LEDs) arranged in rows, and wherein axes of illumination of said LEDs are pointed downward at predefined elevation angles with respect to horizontal such that each of said rows corresponds to a different predefined elevation angle; and
  a single camera positioned substantially to one side of said substantially cylindrical illuminator to capture a single image of at least a portion of said interior surface of said substantially cylindrical object via light reflected directly from said interior surface of said substantially cylindrical object to said camera.

17. The system of claim 16 further comprising a computer-based platform interfacing to said camera to receive, in digital form, said single image.

18. The system of claim 17 wherein said computer-based platform analyzes said single image to identify any defects of at least a portion of said interior surface of said substantially cylindrical object.

19. The system of claim 17 wherein said camera interfaces to said computer- based platform via an Ethernet connection.

20. The system of claim 17 wherein said computer-based platform comprises a personal computer (PC).

21. The system of claim 16 wherein a central axis of a lens of said camera and a central axis of said substantially cylindrical illuminator are substantially aligned along a single central axis of said system.

22. The system of claim 16 wherein said substantially cylindrical object comprises a beverage can wherein a top of said beverage can is substantially open.

23. The system of claim 16 wherein said camera comprises a digital camera.

24. The system of claim 16 wherein said system images in excess of 2000 of said objects per minute as said objects pass within a field of view of said system one after another.

25. The system of claim 17 wherein said single image comprises at least 1000 pixels by 1000 pixels.

26. A method of constructing a system to image an interior surface of at least one substantially cylindrical object, said method comprising:
  positioning a substantially cylindrical illuminator substantially to one side of an opening of a substantially cylindrical object to be imaged to illuminate at least a portion of an interior surface of said object, wherein said substantially cylindrical illuminator includes a plurality of light emitting diodes (LEDs) arranged in rows, and wherein axes of illumination of said LEDs are pointed downward at predefined elevation angles with respect to horizontal such that each of said rows corresponds to a different predefined elevation angle;
  positioning a truncated conical mirror substantially within an open interior region of said illuminator to reflect an image of at least a portion of said interior surface of said object;
  positioning a single camera substantially to one side of said illuminator and said mirror to capture a single image of at least said interior surface of said object via light reflected at least directly from at least a portion of said interior surface of said object to said camera and from said mirror to said camera;
  aligning central axes of said illuminator, said mirror, and said camera with a central axis of said object to be imaged; and
  mounting said aligned illuminator, mirror, and camera to fix the alignment.

27. The method of claim 26 further comprising interfacing said single camera to a computer-based platform for storing and analyzing said single image.

28. The method of claim 27 further comprising providing electrical power to said camera, said illuminator, and said computer-based platform.

29. A system for imaging an interior surface of at least one substantially cylindrical object, said system comprising:

a substantially cylindrical illuminator, positioned substantially to one side of an opening of a substantially cylindrical object to be imaged, to illuminate at least a portion of said interior surface of said substantially cylindrical object, wherein said substantially cylindrical illuminator comprises an arrangement of a plurality of light emitting diodes (LEDs), and wherein axes of illumination of said plurality of LEDs point substantially toward an interior cylindrical volume circumscribed by said arrangement, and wherein horizontal directional components of illumination of said plurality of LEDs, in any imaginary horizontal plane crossing through said substantially cylindrical illuminator, are pointed such that said horizontal directional components of illumination do not intersect an imaginary vertical central axis of said interior cylindrical volume;

a truncated conical mirror positioned substantially within an open interior region of said substantially cylindrical illuminator to reflect an image of at least a portion of said interior surface of said substantially cylindrical object; and a single camera positioned substantially to one side of said substantially cylindrical illuminator and said truncated conical mirror to capture a single image of at least said interior surface of said substantially cylindrical object via light reflected at least directly from at least a portion of said interior surface of said substantially cylindrical object to said camera and from said truncated conical mirror to said camera.

* * * * *